Dec. 5, 1972 C. G. KLEHM Plant Pat. 3,264
PEONY PLANT
Filed Feb. 1, 1971
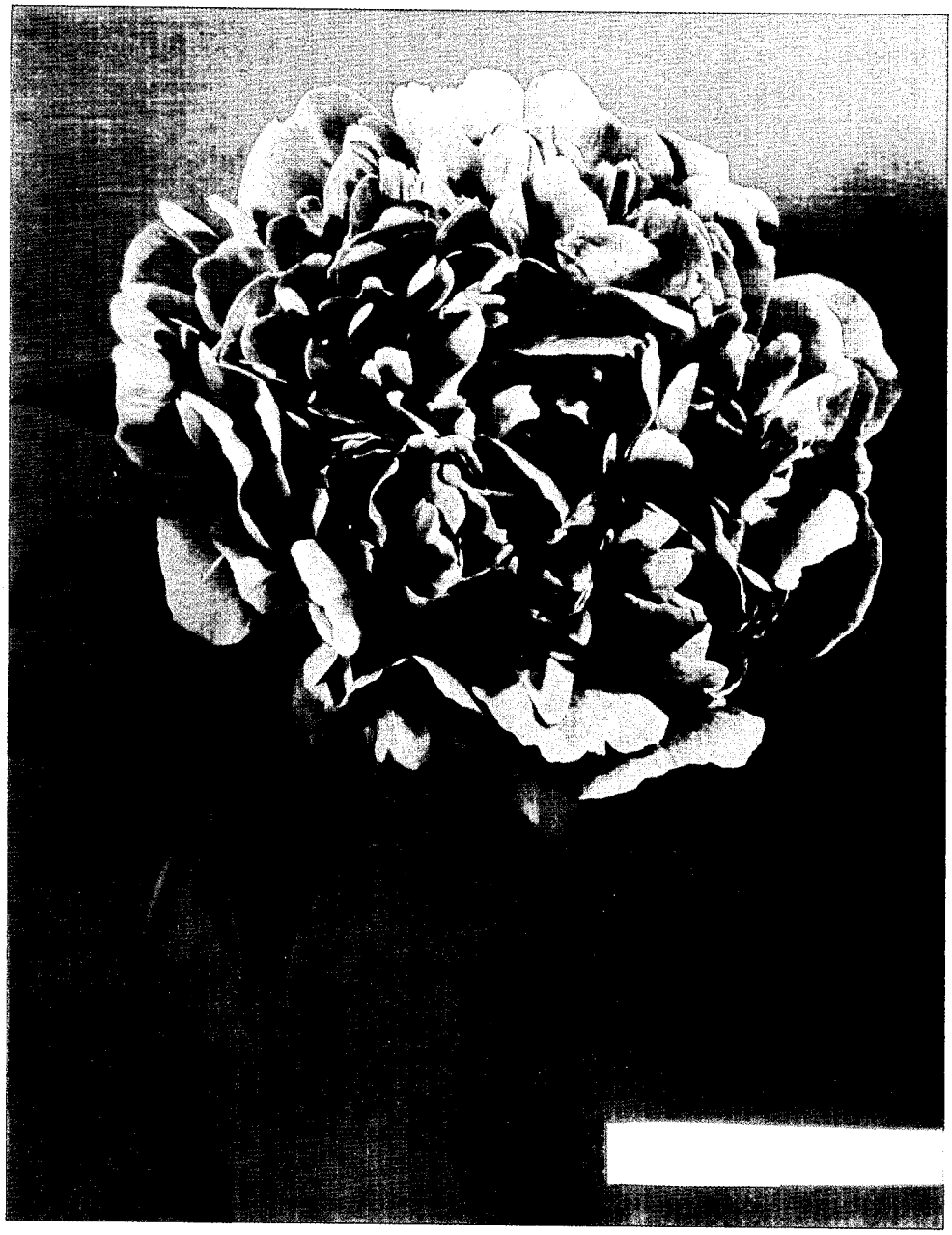
Inventor.
Carl G. Klehm
By: Robb & Robb
Attorneys.

United States Patent Office

Plant Pat. 3,264
Patented Dec. 5, 1972

3,264
PEONY PLANT

Carl G. Klehm, 2 E. Algonquin Road,
Arlington Heights, Ill. 60005

Filed Feb. 1, 1971, Ser. No. 111,771
Int. Cl. A01h 5/00
U.S. Cl. Plt.—68 1 Claim The present invention relates to a new and distinct variety of peony plant of the species botanically known as *Paeonia lactiflora*, which was originated by me by crossing an unnamed and unpatented "bull" type peony seedling, identified in my breeding records as No. 69J, with the peony variety known as "Mons. Jules Elie" (unpatented), the unnamed seedling being the male parent and "Mons. Jules Elie" being the female parent.

My new variety resulted from an extensive and prolonged program of breeding and testing conducted by me in an effort to produce new and improved or unique peony varieties, and was selected as one of many outstanding varieties resulting from this breeding program because of its unique combination of the following principal characteristics which distinguish the new variety from its parents, as well as from all other peony varieties of which I am aware:

(1) A rather fine textured, balanced and vigorous root system which produces thick, strong and relatively weather-resistant stems;

(2) Attractive and healthy, succulent, clean and spotless foliage of dark green color;

(3) Dependability of flower bud formation and opening thereof, with a dependable relatively early blooming season;

(4) A relatively large flower size having a fully double rose-type flower form;

(5) A distinctive and attractive vivid rose pink flower color overlaid on a soft red background and with a silver edging on the extremities of the flower petals; and (6) A suitability for use with other perennial plantings such as for borders and backdrops for other plant settings, as well as suitability for attractive cut flowers.

Asexual reproduction of my new peony variety by root division, as performed by me in my nursery located at Arlington Heights, Ill., shows that the foregoing characteristics and distinctions come true to form and are established and transmitted through succeeding propagations.

The accompanying drawing shows typical specimens of the vegetative growth and flowers of my new variety, as depicted in color as nearly true as it is reasonably possible to make the same in a color illustration of this character.

The following is a detailed description of the new variety, with color terminology in accordance with the Horticultural Colour Chart (1966 edition), published by The Royal Horticultural Society, of London, England, as based on specimens grown and observed by me at Arlington Heights and Barrington, Ill.

Breeding: Seedling.
- *Seed parent.*—"Mons. Jules Elie."
- *Pollen parent.*—An unnamed seedling identified as No. 69J.

Propagation: Holds its distinguishing characteristics through succeeding propagations by root division.

FLOWER

Blooming habit: Annual; early.

Blooming season: Considered extremely early, and flowers open before any other major lactiflora species when grown in the same region under the same conditions; usually blooms at least 2 to 4 days earlier than the standard "Mons. Jules Elie."

Bud:
- *Size.*—Large.
- *Form.*—Slightly crinkled.
- *Color.*—Rose Red, Fan Z, Plate 588′.
- *Sepals.*—Crinkled, with uneven edge. Color: Green.
- *Calyx.*—Polysepalous.
- *Opening.*—Opens easily and without malformities.

Bloom:
- *Size.*—Medium large, normally averaging from about 6 inches to 7½ inches in diameter when fully expanded.
- *Borne.*—Singly; usally one main bud per stem, with from 2 to 4 auxiliary buds.
- *Stems.*—Strong; tall (about 30 to 32 inches).
- *Form.*—Double-rose type, with 2 or 3 rows of guard petals.
- *Petalage.*—Double.
- *Color.*—Vivid rose pink, overlaid on soft red background and with silver edging on extremities of petals, corresponding to blends of Fan Z, Plate 58B, Fan 1, Plate 55A and Fan 1, Plate 49D.
- *Variegations.*—None.
- *Discolorations.*—Usually none, but relative intensity of the sun does affect the color blending and the silver petal edging.

Petals:
- *Texture.*—Medium thick.
- *Appearance.*—Shiny and multitudinous.
- *Form.*—Slightly crinkled and notched.
- *Arrangement.*—Imbricated.
- *Persistence.*—Above average.
- *Fragrance.*—Slight.
- *Lasting qualities.*—Above average.

REPRODUCTIVE ORGANS

Stamens, anthers: Present.
Stamens, filaments: Present.
Pollen: Present and viable.
Styles: None.
Stigmas: None.
Ovaries: None.
Fruit: None.

PLANT

Form: Bush.
Growth: Healthy; strong, early and vigorous.
Foliage:
- *Leaflets.*—5 or 6 in number.
- *Size.*—Large.
- *Quantity.*—Average.
- *Color.*—Deep bottle green, Fan 3, Plate 135A′.
- *Shape.*—Elliptically acute.
- *Texture.*—Glossy, with pronounced veins.
- *Edge.*—Smooth.
- *Serrations.*—None.
- *Leaf stem.*—Thick; succulent.
- *Stipules.*—None.
- *Disease resistance.*—Resistant to leaf blotch and other bacterial peony diseases, as determined by comparison with other varieties for many years as grown at Arlington Heights and Harrington, Ill.

GENERAL OBSERVATIONS

The early blooming habit and unusual flower color combinations of my new variety, as described in the foregoing, are distinctively unique in the Paeonia genus.

I claim:

1. A new and distinct variety of peony plant of the species botanically known as *Paeonia lactiflora,* substantially as herein shown and described, characterized particularly as to novelty by the unique combination of a rather fine textured, balanced and vigorous root system which produces thick, strong and relatively weather-resistant stem, attractive and healthy, succulent, clean, and spotless foliage of dark green color, dependability of flower bud formation and opening thereof, with a dependable relatively early blooming season, a relatively large flower size having a fully double rose-type flower form, a distinctive and attractive vivid rose pink flower color overlaid on a soft red background and with a silver edging on the extremities of the flower petals, and a suitability for use with other perennial plantings such as for borders and backdrops for other plant settings, as well as suitability for attractive cut flowers.

No references cited.

ROBERT E. BAGWILL, Primary Examiner